United States Patent [19]
Xanthopoulos

[11] Patent Number: 5,044,949
[45] Date of Patent: Sep. 3, 1991

[54] DENTAL ARTICULATOR

[76] Inventor: George Xanthopoulos, 8260 E. Arabian Trail,, Scottsdale, Ariz. 85258

[21] Appl. No.: 487,203

[22] Filed: Mar. 1, 1990

[51] Int. Cl.⁵ .............................................. A61C 11/00
[52] U.S. Cl. ....................................... 433/58; 433/60
[58] Field of Search ...................... 433/58, 57, 59, 60, 433/65

[56] References Cited

U.S. PATENT DOCUMENTS

| | | | |
|---|---|---|---|
| 1,291,919 | 1/1919 | Kerr | 433/58 |
| 1,320,583 | 11/1919 | Stanbrough | 433/58 |
| 4,496,320 | 1/1985 | Hwang et al. | 433/60 |
| 4,734,033 | 3/1988 | Huffman | 433/60 |
| 4,946,388 | 8/1990 | Bolton | 433/65 |

Primary Examiner—Gene Mancene
Assistant Examiner—Adriene B. Lepiane
Attorney, Agent, or Firm—Tod R. Nissle

[57] ABSTRACT

A dental articulator. The articulator holds a dental model of the upper teeth of a patient in selected orientations with respect to a dental model of the patient's lower teeth and permits the dental models to be readily removed from and reattached to the articulator in a desired selected orientation between the models.

7 Claims, 5 Drawing Sheets

DENTAL ARTICULATOR

This invention relates dental articulators.

More particularly, the invention relates to an articulator which holds a dental model of the upper teeth of a patient in selected orientations with respect to a dental model of the patient's lower teeth and which permits the dental models to be readily removed from and reattached to the articulator while maintaining a desired selected orientation between the models of the upper and lower teeth.

In another respect, the invention relates to molding apparatus which can be utilized to form dental molds of the upper and lower teeth of a patient while maintaining a desired orientation and bite between the upper and lower teeth.

Dental articulators are well known in art. See, for example, U. S. Pat. Nos. 4,481,162 and 4,382,787 to Huffman and 2,138,254 to Mink. Articulators are devices which simulate the upper and lower jaws of a patient. The working part and the opposing part of a dental model are mounted on the articulator. The working part of the dental model duplicates one of the upper and lower sets of teeth in a patient's mouth. The opposing part of the dental model duplicates the other of the upper and lower sets of teeth. A conventional articulator includes a pair of arms which each have a rear portion and a forward portion. The forward portion of each arm is adapted to be attached to one of the dental models. The rear portion of the arms are pivotally or otherwise interconnected so that movement of the articulator arms simulates the movement of the upper and lower jaws of a patient.

A problem which must be solved by an articulator is maintaining the model of the lower teeth in the proper orientation with respect to the model of the upper teeth so the models, when used in combination on the articulator, accurately reproduce the registration and bite of the teeth. In many prior art articulators this problem is solved by first attaching a model, say the model of the lower teeth, to one arm (the lower arm) of the articulator. The model is attached to the arm with plaster. The other model, of the upper teeth, is placed on the model of the lower teeth so that the tips of the upper and lower teeth properly register and duplicate the bite of the patient. The model of the upper teeth is then attached to the other arm (the upper arm) of the articulator with plaster while the bite registration between the upper and lower teeth of the models is maintained. After the plaster dries, the arms of the articulators, with the models attached, can be moved to simulate movement of the teeth in the mouth of the patient. One disadvantage of this procedure is that mixing plaster takes time, as does drying the plaster which is used to attach a dental mold to the articulator. Further, plaster produces a fine powder which coats drawers, shelves and countertops in a dental lab and which requires dental technicians to wear masks to avoid inhaling the powder. The use of plaster causes a dental lab to incur significant expense in cleaning and labor during the production of dental bridges and crowns. Consequently, having to utilize plaster during the mounting of dental molds is undesirable; however, it is a practice which has largely endured over the years.

Another problem which must be addressed by an articulator is the accurate simulation of the movement of the upper and lower jaws of the mouth. Most conventional articulators are relatively simplistic in structure and only approximate one or more of the three basic movements of the lower jaw. The first such movement of the lower jaw occurs when an individual opens and closes his mouth, and is termed rotational movement because the lower jaw rotates about the points at which the lower jaw is attached to the skull. The second such movement of the lower jaw occurs during chewing when the lower jaw is moved to displace the cusps of the lower teeth over the cusps of the upper teeth. This second movement is termed lateral excursion. The third movement occurs when the lower jaw is displaced rearwardly toward the neck. During this rearward movement the lower incisors move away from the upper incisors. This rearward movement of the lower jaw is termed retrusive movement.

Articulators exist which closely approximate the three basic movements of the lower jaw but such articulators ordinarily are very expensive and, because of their expense, are not practical for wide scale use by dentists and dental laboratories.

A disadvantage associated with conventional articulators is that once dental models are attached to the articulator with plaster, the models cannot, practically speaking, be removed. When the dental models are forwarded to the dentist, the articulator on which the models are mounted must also be forwarded to the dentist. This means dental laboratories expend considerable amounts of money in maintaining an adequate supply of articulators. It also means that if the dental laboratory does not have an articulator available, the laboratory is prevented from mounting the dental molds to properly align the cusps of the lower teeth with the cusps of the upper teeth.

Accordingly, it would be highly desirable to provide an improved dental articulator and apparatus for producing dental models which would eliminate the use of plaster in producing dental models and in attaching the models to the articulator and which would, while being relatively simple in structure, simulate the three basic movements of the jaw.

It would also be highly desirable to provide an improved dental articulator and apparatus for producing dental models which would enable the cusps of the upper and lower teeth replicas in a dental model to be properly aligned without requiring the use of an articulator.

Therefore, it is a principal object of the invention to provide an improved method and apparatus for producing dental models and for producing a dental articulator on which the dental models are mounted.

A further object of the invention is to provide an improved method and apparatus for producing dental models and mounting the models on an articulator, the improved method and apparatus not requiring the use of plaster.

Another object of the instant invention is to provide an improved articulator which is of simple construction and simulates the three basic movements of the lower jaw of a human being.

Still another object of the invention is to provide an improved method and apparatus for making dental models and mounting the models on an articulator, the improved method and apparatus permitting dental models to be readily removed from an articulator in a dental lab and transported to a dentist's office to be mounted on a second articulator in the dentist's office.

Yet another object of the invention is to provide an improved method and apparatus of the type described which would, without requiring that the dental models be mounted on an articulator, enable the cusps of the upper and lower teeth to be properly aligned with respect to one another to duplicate the registration and bite of the teeth.

These and other, further and more specific objects and advantages of the invention will be apparent to those skilled in the art from the following detailed description thereof, taken in conjunction with the drawings, in which:

Briefly, in accordance with my invention, I provide an improved dental articulator for mounting a dental model. The dental model includes a lower part and an upper part. The lower part includes replications of the lower teeth of a patient's mouth. The upper part includes replications of the upper teeth of a patient's mouth. The dental articulator includes a base means including a forward portion shaped and dimensioned to receive the lower part of the dental model; an upper member including a forward portion shaped and dimensioned to receive the upper part of the dental model, the upper member having first and second operative positions; and, connecting means for interconnecting the base means and the upper member in spaced apart relationship. The connecting means includes at least one support arm attached to and outwardly extending from the base means; shaft means extending from said support arm, spaced apart from said base means, and having a longitudinal axis spaced apart from the forward portion of the upper member; a slot formed in the upper member, slidably engaging the shaft means, and having a back inner stop portion; and, spring means interconnecting the upper member and the shaft means. The spring means extends outwardly from the shaft means and has a selected load to hold the upper member in the first operative position with the back inner stop portion of the slot against at least one of the pair consisting of the spring means and the shaft means. The slot and the shaft means are shaped and dimensioned such that when a lateral force generally parallel to and spaced apart from the longitudinal axis of the shaft means and having a selected magnitude is applied to the forward portion of the upper member, a torque is produced on the upper member. The torque causes the upper member to move from the first operative position to the second operative position; causes the slot to pivot with respect to and move over the shaft means and at least a portion of the stop portion to move away from the shaft means; and, causes the loading of the spring means to be altered. The slot and shaft means can be shaped and dimensioned such that when a transverse force which acts in a direction perpendicular to the lateral force, which acts in a direction perpendicular to and spaced apart from the longitudinal axis of the shaft means, and which has a selected magnitude is applied to the forward portion of the upper member a rotational torque is produced which acts on the upper member. The rotational torque causes the upper member to rotate around the longitudinal axis from the first operative position to a third operative position, but does not alter the load on the spring means. The slot and shaft means can also be shaped and dimensioned such that when a displacement force which acts in a direction perpendicular to the transverse force, which acts in a direction perpendicular to, toward, and passing through the longitudinal axis of the shaft means, and which has a selected magnitude, is applied to the forward portion of the upper member, the forward portion is pushed toward the longitudinal axis. When the forward portion is pushed toward the longitudinal axis the upper member moves from the first operative position to a fourth operative position, and the loading of the spring means is altered.

In another embodiment of my invention, I provide improved molding apparatus for forming an opposing part of a dental model. The dental model includes the opposing part and a working part. The opposing part includes a base; and, affixed to the base, replications of one of a pair of sets of teeth in the group consisting of the upper set of teeth in a patient's mouth and the lower set of teeth in the patient's mouth. The working part includes a base; and, affixed to the base of the working part, replications of the other of the pair of sets of teeth in the group consisting of the upper set of teeth in a patient's mouth and the lower set of teeth in the patient's mouth. The opposing and working parts are attached to an articulator. The articulator includes a base means including a forward connector portion shaped and dimensioned to detachably receive the lower part of the dental model; an upper member including a forward connector portion shaped and dimensioned to detachably receive the upper part of the dental model; and, connector means for interconnecting the base means and the upper member in spaced apart relationship. The improved molding apparatus includes a mold for forming from a pourable hardenable compound deposited therein said base of the lower part of the dental model, the mold including a sidewall for defining the perimeter of the mold cavity and having an upper edge for defining the opening to the mold cavity, a substrate extending intermediate the sidewall and defining the bottom of the mold cavity, and an opening formed in the sidewall; first attachment means including a connector member shaped and dimensioned to be inserted in said opening, anchor means extending from the connector member within the perimeter of the mold cavity to be at least partially covered by and to engage pourable hardenable compound poured in the mold cavity, and means for detachably connecting said first attachment means to the forward connector portion of one of the pair consisting of the base means and the upper member of the articulator; at least one elongate positioning post having a longitudinal axis and a lower end and an upper end, the lower end being received by and anchored in an opening formed in the group consisting of the sidewall, the substrate, and the first attachment means; dental model means including the working part of the dental model, the one of the pair of sets of teeth removably affixed to the other of the pair of sets of teeth to duplicate the bite between the one and the other of the pair of sets of teeth, and, second attachment means attached to the base of the working part and shaped and dimensioned to slidably engage and move down the positioning post. When the second attachment means slidably moves down the positioning post, the second attachment means maintains the base of the working member in a selected orientation with respect to the bottom of the mold cavity, maintains the one of the sets of teeth above the bottom of the mold cavity and intermediate the bottom and the working part of the model means, and imbeds a portion of the one of the pair of sets of teeth in hardenable compound poured in the mold, the one of the pair of sets of teeth being anchored in the compound when the compound hardens.

Turning now to the drawings, which depict the presently preferred embodiments of the invention for the purpose of illustrating the practice thereof and not by way of limitation of the scope of the invention, and in which like reference characters refer to corresponding elements throughout the several views, FIGS. 1 to 5 illustrate a dental articulator constructed in accordance with the principles of the invention and including base means 20, upper member 30, and connector means or support arms 40 and 41. Connector means 40 and 41 each comprise a support arm. The support arms interconnect base means 20 and upper member 30 in spaced apart relationship. Connector means or support arm 40 outwardly extends from panel member 21 of base means 20. Arm 40 includes hollow cylindrical sleeve 41A which is fixedly connected to panel member 21. A plurality of slits or cuts 42 are formed in sleeve 41A parallel to the longitudinal axis of sleeve 41. The longitudinal axis of sleeve 41 is perpendicular to the horizontal plane in which panel member 21 lies. Sleeve 41A is externally threaded (not visible) and carries knurled, internally threaded generally cylindrical adjustment knob 43. When knob 43 is turned in the direction of arrow A it compresses sleeve 41A to reduce the size of slits 42 and press sleeve 41A against shaft 44 which is slidably received by sleeve 41A. When knob 43 is turned in the direction of arrow B, the compression on sleeve 41A is released so that shaft 44 can readily be slidably pulled free from sleeve 41 in the direction of arrow C. The structure of support arm 40 is identical to the structure of support arm 41. Consequently, as will be appreciated, support arms 40 and 41 permit the vertical distance between base means 20 and upper member 30 to be readily adjusted.

Figure 1:
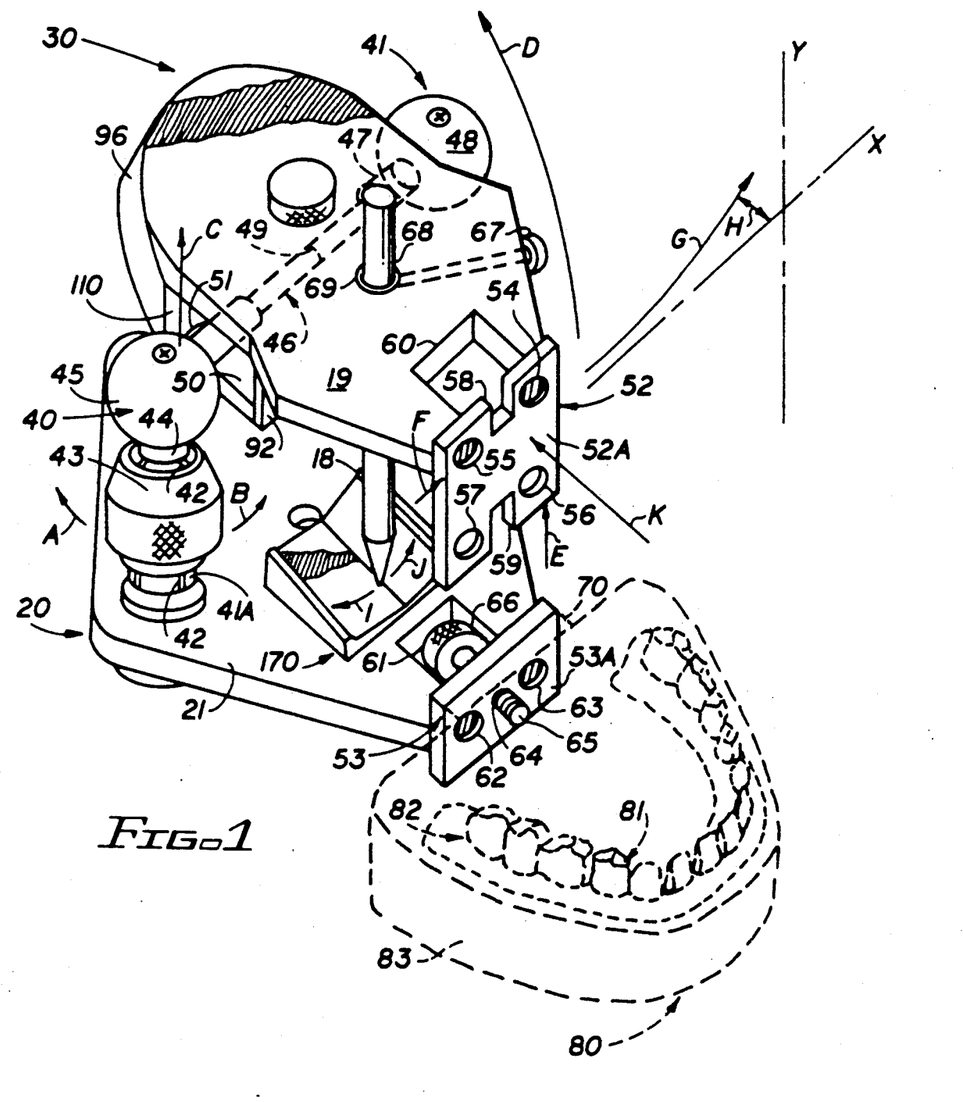
FIG. 1 is a perspective view illustrating a dental articulator constructed in accordance with the principles of the invention.

Spherical member 45 of support arm 40 is fixedly attached to shaft 44 and fixedly receives the larger diameter end of shaft 46. The larger diameter end of shaft 47 is fixedly received by spherical member 48 of support arm 41. The smaller diameter ends of shafts 46 and 47 are welded or otherwise connected as indicated by reference character 49 in FIG. 1. Alternatively, shafts 46 and 47 can be the parts of a unitary shaft. Shafts 46 and 47 extend through a slot 50 formed in upper member 30. In FIG. 1, shaft 46 is shown bearing against the arcuate back inner stop portion 51 of slot 50.

The forward portion 52 of upper member 30 is shaped and dimensioned to receive the attachment means connected to the upper part (or lower part) of a dental model manufactured in accordance with the invention. The forward portion 53 of the base means 20 is shaped and dimensioned to receive the attachment means connected to the lower part (or the upper part) of a dental model manufactured in accordance with the invention. Cylindrical openings 54 to 56 are formed in portion 52, along with U-shaped slots 58 and 59. U-shaped slot 60 bounds and houses the knurled head (not shown) of a screw. The threaded portion of the screw extends through slot 58 to engage the attachment means of the upper part of a dental model. The screw can also, if desired, be moved downwardly from U-shaped slot 60 such that the threaded portion of the screw extends outwardly through slot 59 to engage the attachment means of the upper part of a dental model.

Cylindrical openings 62 and 63 are formed in portion 53, along with cylindrical aperture 64. U-shaped slot 61 bounds and houses the knurled head 66 of a screw. The threaded portion or shank 65 of the screw extends through aperture 64 to engage the attachment means of the lower part of a dental model.

The conical tip of shaft 68 slides over the sloped surfaces of member 170 in the manner indicated by arrows I and J. The surfaces of member 170 which the conical tip of shaft 68 contacts and slides over are at a slope from the horizontal of about 15°. In FIG. 1. axis X is the horizontal axis and axis Y is the vertical axis. Set screw 67 is used to position shaft 68 in aperture 69. When set screw 67 is loosened, shaft 68 can be slidably moved through aperture 69 in directions of travel parallel to vertical axis Y.

In FIG. 1, force F acts against portion 52 in a direction which is parallel to the longitudinal axis of shafts 46 and 47 and is parallel to horizontal axis X. Force F generates a torque on portion 52 and upper member 30. As will be further described, when the magnitude of force F is sufficient, portion 52 is displaced in the direction of arrow G and slot 50 pivots about shafts 46 and 47. The movement of member 30 in the direction of arrow G simulates the lateral excursion of the lower jaw with respect to the upper jaw.

In FIG. 1, force E acts against portion 52 in a direction which is parallel to vertical axis Y, and perpendicular to force F and to the longitudinal axis of shafts 46 and 47. Force E generates a rotational torque of force on portion 52 and member 30. When the magnitude of force E is sufficient, portion 52 is upwardly displaced in the direction of arrow D as member 30 rotates about shafts 46 and 47 in the same manner that a door rotates about its hinges. The movement of member 30 in the direction indicated by arrow D simulates the rotational movement of the lower jaw with respect to the upper jaw when the mouth of a human being is opened.

In FIG. 1, force K acts against portion 52 in a direction which is perpendicular to forces E and F, is perpendicular to axes X and Y, and passes through the longitudinal axis of shafts 46 and 47. When the magnitude of force K is sufficient, portion 52 and member 30 are rearwardly displaced in the direction of arrow K. This rearward movement of member 30 is used to simulate the reclusive movement of the lower jaw with respect to the upper jaw of a human being.

The lower part of a dental model 80 is indicated in dashed outline in FIG. 1 and includes replicas of the lower teeth 81 and gums 82 of a patient. The replica 82 of the lower gums adheres to a generally triangular base 83. Attachment means 70 is connected to the rear part of base 83. As will be described, attachment means 70 includes a pair of outwardly projecting cylindrical nubs 71 and 72 which are slightly smaller than and are slidably received by opening 62 and 63. Means 70 also includes an internally threaded aperture 125 into which shank 65 is threaded to secure means 70 snugly adjacent portion 53.

In FIG. 1, the upper planar surface 19 is parallel to axis X. When a force F is applied to portion 52 and member 30 is displaced in the direction of arrow G, member 30 and surface 19 begin to tilt with respect to axis X. The maximum amount of tilt achieved by surface 19 with respect to axis X is typically in the range of 10° to 15° C. This maximum amount of tilt is achieved when the conical tip of shaft 68 has moved as far as permitted in the direction of arrow J and has contacted stop ledge 18 of member 170. If a force parallel to and collinear with force F is applied to portion 52 in FIG. 1 and acts in a direction opposite that of force F, portion 52 and member 30 move in a direction opposite that of arrow G and again will achieve maximum tilt in the range of 10° to 15° C. When portion 52 moves in a direction opposite that of arrow G, the conical tip of shaft 68 moves along member 170 in the manner indicated by arrow I.

Figure 2:
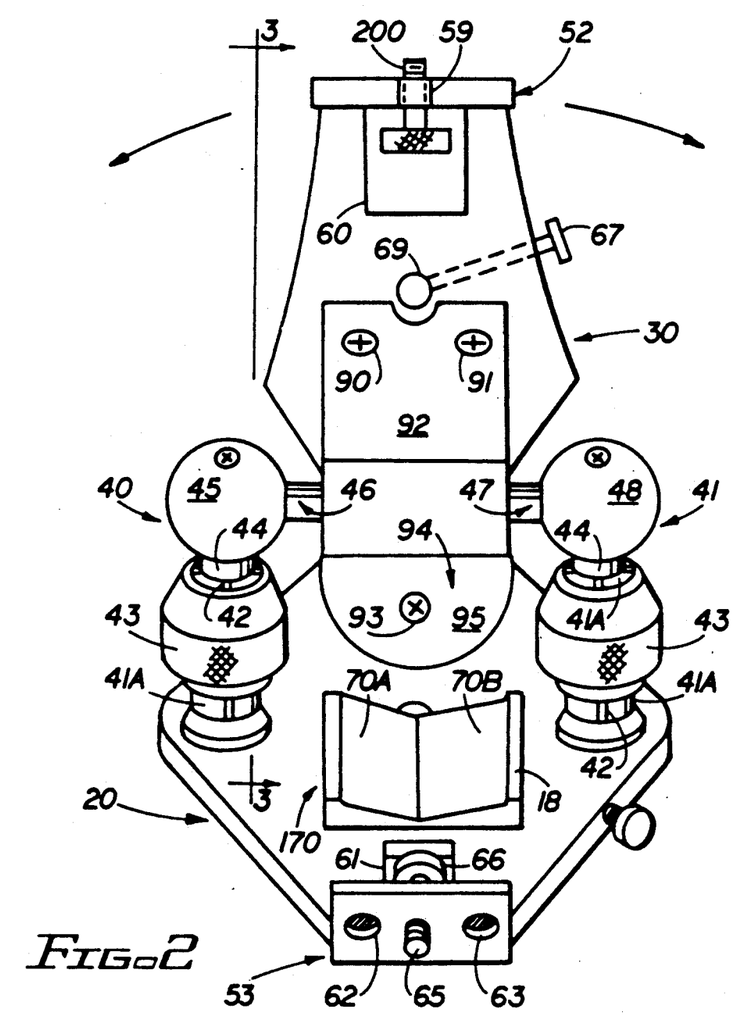
FIG. 2 is a front perspective view illustrating the articulator of FIG. 1 after the upper member of the articulator has been rotated upwardly to a generally vertical orientation.

In FIG. 2, the upper member 30 has been rotated from its position in FIG. 1 upwardly in the direction of arrow D to a position in which flat planar surface 19 is generally vertically oriented and parallel to the vertical axis Y. The sloped surfaces 70A and 70B are more clearly seen in FIG. 2, as are screws 90 and 91 securing panel member 92 in position. Screw 93 fixes housing or cap 94 in position on upper member 30. Cap 94 includes flat panel 95 with a semicircular edge and includes a semicircular wall 96 which is normal to panel 95. Member 170 is fixedly attached to panel member 92.

Figure 3:
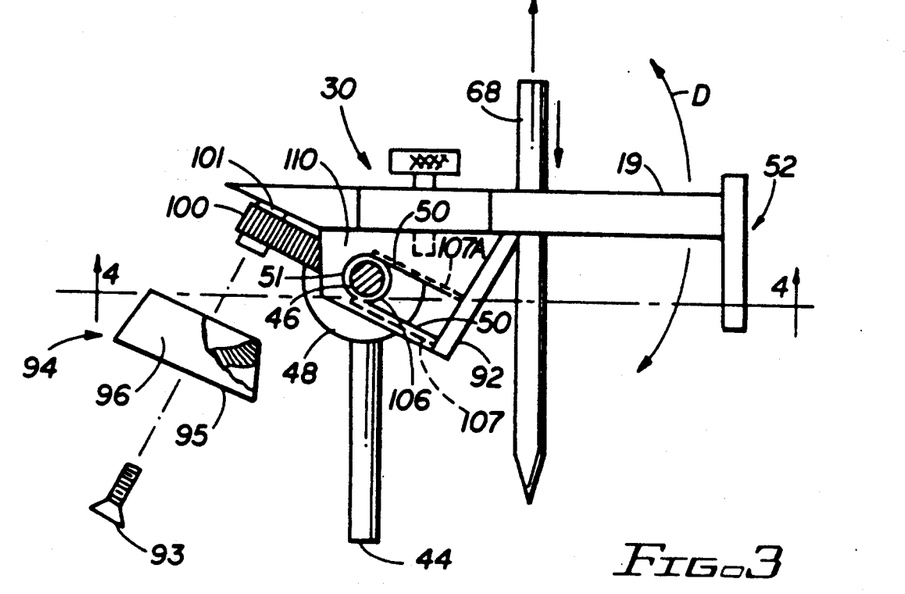
FIG. 3 is a side view of the upper member of the articulator of FIG. 1 illustrating further construction details thereof.

In FIG. 3, cap 94 is shown after screw 93 has been removed and cap 94 moved away from member 30 to expose spring 100 extending around fixed, rigid cylindrical member 101. An internally threaded aperture 102 formed in member 101 receives the externally threaded shank of screw 93 to hold cap 94 in place in the manner shown in FIGS. 1 and 2.

In FIG. 3, the attachment of ends 16 and 17 of spring 100 to the smaller diameter portions of shafts 46 and 47 is seen. Also in FIG. 4, panel member 92 has been removed, exposing the internally threaded apertures 103 and 104 which receive screws 90 and 91 of plate 92. Sleeve 105 with a spherically shaped outer surface is slidably carried by the smaller diameter portion of cylindrical shaft 46. Sleeve 106 with a spherically shaped outer surface is slidably carried by the smaller diameter portion of cylindrical shaft 47. The outer spherically shaped surface of sleeve 105 slides or rolls along groove 107 in slot 50 while the outer spherically shaped surface of sleeve 106 slids or rolls along the groove 108 in slot 50. The outer spherically shaped surface of sleeve 105 also slides or rolls along an arcuate groove 107A which is formed in slot 50 of member 110 and which is parallel, spaced apart from and opposed to arcuate groove 107. Similarly, the outer spherically shaped surface of sleeve 106 also slides or rolls along an arcuate groove 108A which is formed in slot 50 of member 110 and is parallel, spaced apart from and opposed to arcuate groove 108. The outer spherical surfaces of sleeves 105 and 106 are shaped and contoured to conform to the shape of grooves 107 and 107A and 108 and 108A, respectively. Sleeves 105 and 106 have apertures formed therethrough which permit the sleeves to slidably move along the smaller diameter portions of shafts 46 and 47 but which prevent sleeves 105 and 106 from moving onto and sliding along the larger diameter portions of shafts 46 and 47. By way of example of the operation of sleeves 105 and 106, assume that in FIG. 4 a force F of sufficient magnitude is applied to move portion 52 and member 30 in the direction of arrow G while shafts 46 and 47 remain stationery. When portion 52 begins moving in the direction of arrow G, sleeve 105 remains in contact with the back inner stop portion 51 of slot 50 but begins to slide along the smaller diameter portion of shaft 46 toward sleeve 106. Further, when portion 52 begins to move in the direction of arrow G along with the forward portion of member 30, the section of the back inner stop portion 51 adjacent sleeve 106 begins moving in the direction of arrow M and loses contact with sleeve 106. Sleeve 106, when said section of the back inner stop portion 51 begins to move away from contact with sleeve 106 and in the direction of arrow M in FIG. 4, begins to roll or slide along opposed arcuate grooves 108 and 108A. When force F is released or is no longer applied to portion 52, then spring 100 causes shafts 46 and 47 to return to the normal operative position with respect to portion 15 which is illustrated in FIGS. 3 and 4.

Figure 4:
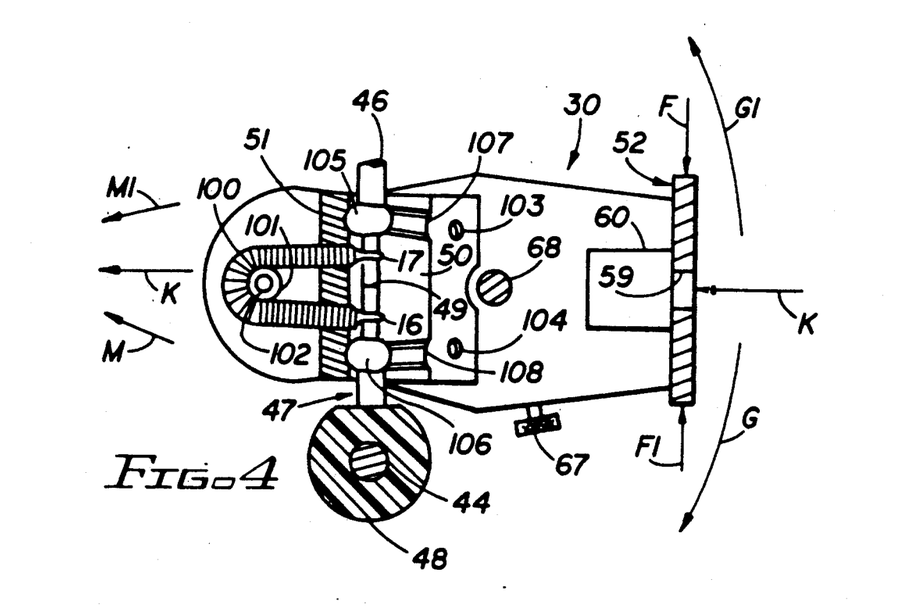
FIG. 4 is a bottom view illustrating the upper member of the articulator depicted in FIG. 3.

By way of further example of the operation of sleeves 105 and 106, assume that in FIG. 4 a force F1 of sufficient magnitude is applied to move portion 52 and member 30 in the direction of arrow G1 while shafts 46 and 47 remain fixed. When portion 52 begins moving in the direction of arrow G1, sleeve 106 remains in contact with the back inner stop portion 51 of the slot 50 but begins to slide along the smaller diameter portion of shaft 47 toward sleeve 105. Further, when portion 52 begins to move in the direction of arrow G1 along with the forward portion of member 30, the section of the back inner stop portion 51 which is adjacent sleeve 105 begins moving in the direction of arrow M1 and loses contact with sleeve 105. Sleeve 105, when said section of the back inner stop portion 51 begins to move away from contact with sleeve 105 and in the direction of arrow M1 in FIG. 4, begins to roll or slide along opposing arcuate grooves 107 and 107A. When force F1 is released or is no longer applied to portion 52, then spring 100 causes shafts 46 and 47 to return to their normal operative position with respect to portion 51 which is illustrated in FIGS. 3 and 4.

In FIG. 3, spring 100 is stretched around member 101 and is tensioned. Consequently, spring 100 is loaded and continuously pulls sleeves 105 and 106 against stop portion 51 of groove 50. When portion 52 is displaced in the direction of arrow G, force F is sufficient to overcome the loading of spring 100 and to stretch the portion of spring 100 extending from member 101 to shaft 47. When spring 100 is so stretched, the loading on spring 100 is, of course, altered or, in this case, increased. If desired, a single length of spring could be substituted for spring 100. This single length of spring would extend from member 101 to the point at which shafts 46 and 47 are joined. The single length of spring (or any other spring) could be tensioned. compressed, or under no load.

In FIG. 1, the planar faces 52A and 53A of portions 52 and 53, respectively, are co-planar and, the shortest vertical distance from opening 63 to opening 54 equals the shortest vertical distance from opening 62 to opening 55. The distance between apertures 54 and 55 is equal to the distance between openings 62 and 63. The shape, dimension and size of each of the openings 54, 55, 56, 57, 62 and 63 is equal to the shape, dimension and size of the remaining openings 54, 55, 56, 57, 62 and 63. The distance between openings 56 and 57 equals the distance between openings 54 and 55. The shortest vertical distance from opening 62 to opening 57 equals the shortest vertical distance from opening 63 to opening 56.

FIGS. 5 to 10 illustrate apparatus utilized to make dental models in accordance with the method of the invention A dental model includes an upper part and a lower part. Either the upper part or the lower part ordinarily is the working part, while the remaining of the upper part and the lower part is the opposing part. The working part of the dental model is the part of the model containing the teeth for which the dental model technician is making a crown or for which the technician is making a bridge. As will be described, the technician first makes the working part of the dental model and then makes the opposing part of the dental model.

Figure 5:
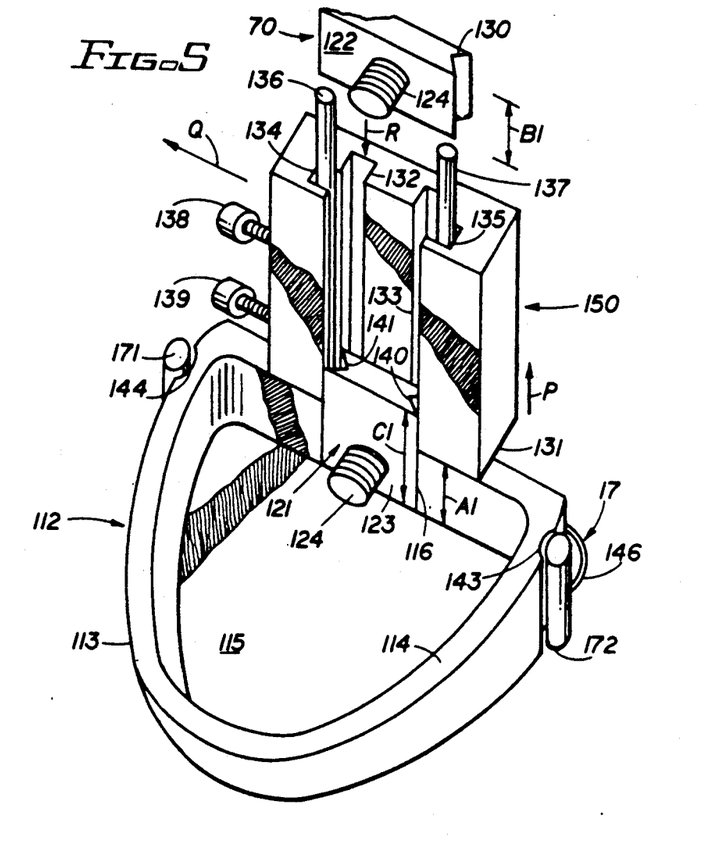
FIG. 5 is a perspective view illustrating apparatus utilized in the manufacture of dental models in accordance with the principles of the invention.

The molding apparatus of FIG. 5 includes a flexible mold 112 for forming from a pourable hardenable compound deposited in the mold the base of either the working part or opposing part of the dental model. Each of the working part and the opposing part of the dental model includes a base and a replica of the upper or lower teeth which is affixed to the base. Mold 112 includes flexible sidewall 113 which defines the perimeter of the mold 112 and which has an upper edge 114 which circumscribes and defines the opening to the mold cavity. Substrate 115 extends across the space intermediate the sidewall 113 and defines the bottom of the mold cavity. An opening 116 is formed in the sidewall 113. On either side of opening 116 are vertically oriented, tapered, V-shaped edges 117 and 118 Opening 116 is shaped and dimensioned to slidably receive either of the connector member 122 and 123 of attachment means 70 and 121, respectively. Attachment means 70 and 121 are substantially identical in shape and dimension except that attachment means 121 includes an upper extension which gives it a height which is greater than that of attachment means 70. In particular, the height of attachment means 70 is identical to the height of sidewall 113. The height of attachment means 70 is indicated by arrows B1 in FIG. 5. The height of sidewall 113 is indicated by arrows A1 in FIG. 5. A1 is equivalent to B1. The height of attachment means 121 is indicated by arrows C1. C1 is greater than A1 or B1. Means 70 and 121 each include anchor means 124 extending from their respective connector member, 122 and 123, within the perimeter of the mold cavity. The externally threaded anchor member 124 is at least partially covered by and engages pourable hardenable compound poured in the cavity of mold 112. Normally, anchor member 124 is completely covered. Each attachment means 70 and 121 includes a pair 71 and 72 of outwardly projecting cylindrical nubs which are slightly smaller than and are slidably received by openings 62 and 63 (or by openings 56 and 57 or by openings 55 and 54).

Attachment means 70 includes a pair of V-shaped vertically disposed parallel grooves 130 and 131. Attachment means 121 includes a pair of V-shaped vertically disposed parallel grooves 140 and 141. Grooves 140 and 141 are equivalent in shape and dimension to grooves 130 and 131 except that grooves 140 and 141 are longer than grooves 130 and 131. The length of grooves 130 and 131 is indicated by arrows B1 in FIG. 5. The length of grooves 140 and 141 is indicated by arrows C1 in FIG. 5. The shortest distance between grooves 130 and 131 is equivalent to the shortest distance between grooves 140 and 141. As indicated in FIG. 5, grooves 140 and 141 are slidably inserted along and conform to V-shaped edges 118 and 117, respectively, of opening 116.

Figure 6:
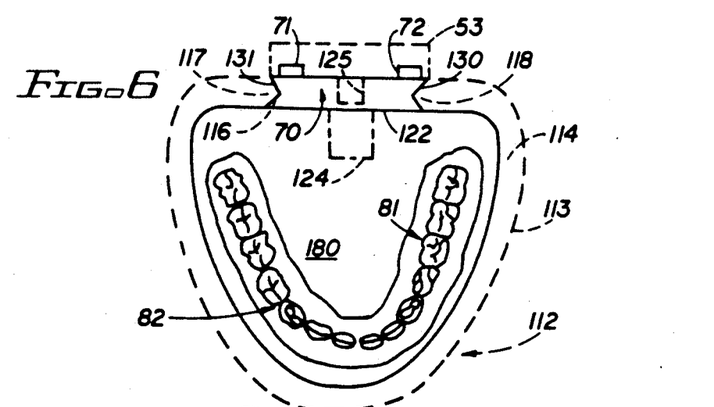
FIG. 6 is a top view illustrating the working part of a dental model produced utilizing the apparatus of FIG. 5.
Figure 7:
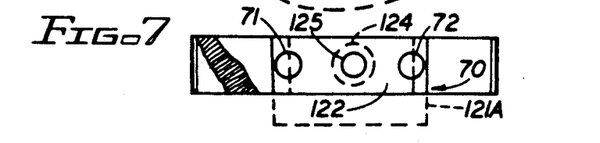
FIG. 7 is a back view of the dental model of FIG. 6.

As a way of demonstrating the close structural similarity of attachment means 70 and 121, it is noted that means 121 is identical to means 70 of FIGS. 6 and 7, except that means 121 is, as indicated by dashed lines 121A in FIG. 7, taller. When means 121 is inserted in opening 116 it extends above edge 114. When means 70 is inserted in opening 116, the top of means 70 is flush with edge 114. When means 121 is inserted in opening 116 the position of anchor means 124 and nubs 71 and 72 with respect to opening 116 and substrate 115 is the same as the position of anchor means 124 and nubs 71 and 72 on means 70 when means 70 is inserted in opening 116.

In FIG. 5, the forward part of the planar bottom 131 of block 150 rests on upper edge 114 of mold 112. Bottom 131 is not fixedly attached to edge 114 and can be upwardly lifted off of edge 114 in the direction of arrow P. Parallel, spaced apart, U-shaped, vertically oriented grooves 132 and 133 are formed in block 150. Parallel, opposed, spaced apart, U-shaped, vertically oriented grooves 134 and 135 are also formed in block 150. Grooves 132, 133, 134 and 135 are parallel to one another. Cylindrical positioning posts 136 and 137 are slidably received by grooves 134 and 135, respectively. Post 136 extends along groove 134 down to the upper edge 114 of mold 112. Post 136 also extends along and contacts groove 141. The lower end of post 136 is slidably frictionally received between the upper portion of groove 141 and the lower portion of groove 134. Post 137 extends along groove 135 down to the upper edge 114 of mold 112. Post 137 also extends along and contacts groove 140. The lower end of post 137 is slidably frictionally received between the upper portion of groove 140 and the lower portion of groove 135. Attachment means 70 can be slidably inserted between the upper ends of posts 136 and 137 in FIG. 5. V-shaped grooves 131 (FIG. 6) and 130 slidably receive the upper ends of posts 136 and 137, respectively. After means 70 is slidably inserted intermediate the upper ends of posts 136 and 137 in FIG. 5, set screws 138 and 139 are tightened to stabilize the block 150—post 136—post 137—mold 112—means 70—means 121 assembly. When set screws 138 and 139 are tightened, the ends of the set screws, which extends through block 150 into groove 134, press against post 136 and tend to cause block 150 to move in the direction of arrow Q against post 137. Wire spring clip 170 extends across the back of mold 112 in FIGS. 5, 8 and 9. Clip 170 compresses the back portion of mold 112 and tends to force edges 117 and 118 of opening 116 into the conforming grooves 141 and 140 of means 121. When means 70 is slidably received by opening (as shown in FIG. 6), spring clip 170 tends to force edges 117 and 118 of opening 116 into the conforming grooves 131 and 130, respectively, of means 70. Spring clip 170 includes cylindrical fingers 171 and 172 received by detents 144 and 143, respectively, of flexible mold 112. Elongate substantially stiff wire clip 146 interconnects fingers 171 and 172.

Figure 10:
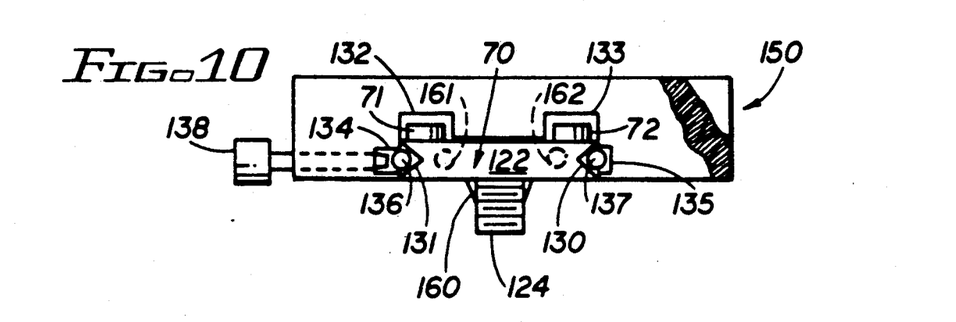
FIG. 10 is a top view of the rectangular post retaining member positioned on the edge of the flexible mold in FIG. 5.

FIG. 10 is a top view of the block 150—means 70—post 136—post 137 assembly of FIG. 5 and illustrates how grooves 132 and 133 are shaped and dimensioned to slidably receive the nubs 71 and 72 on attachment means 70 (or on attachment means 121). FIG. 10 also further illustrates how post 136 extends intermediate groove 131 and groove 134 and how post 137 extends intermediate groove 130 and groove 135. Grooves 131 and 134 function to anchor post 136. Grooves 130 and 135 function to anchor post 137. An alternative means of anchoring post 136 would be to form an aperture in wall 113 or means 70 (or 121). For example, a vertically oriented aperture 161 could be formed in means 70 to slidably receive the lower end of post 136. Similarly, a vertically oriented aperture 162 could be formed in means 70 to slidably receive the lower end of post 136.

Posts 136 and 137 function along with block 150 to maintain means 70 and 121 in a selected orientation with respect to one another, i.e., function to maintain connector members 122 and 123 in a common vertical plane and to maintain the horizontal longitudinal axes of members 122 and 123 in parallel relationship to one another. In FIG. 5, when means 70 and 121 are each interposed intermediate parallel posts 136 and 137, the longitudinal axes or centerlines of cylindrical externally threaded anchor means 124 on members 122 and 123 are also maintained in parallel relationship. If a post 136 had, for example, a hexagonal instead of a cylindrical outer surface and a hexagonal aperture were formed through means 70 parallel to the longitudinal axis of post 136, then when post 136 slidably extended through this hexagonal aperture, means 70 would not be able to rotate and the parallel orientation between member 122 and 123 would be maintained.

Figure 8:
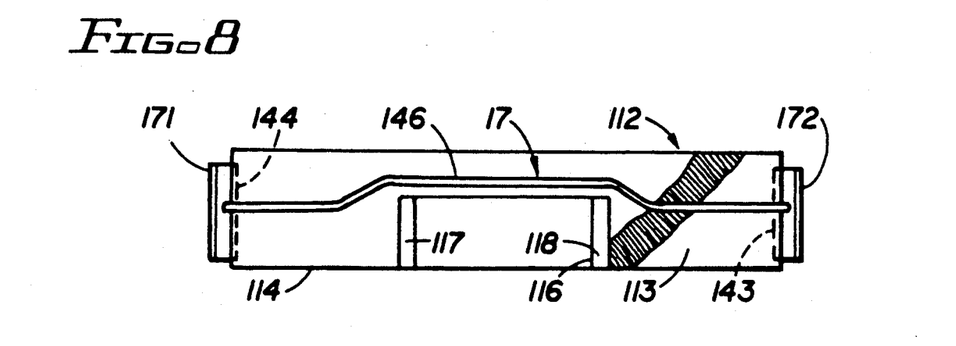
FIG. 8 is a back view of the generally triangular flexible mold of FIG. 5 illustrating the retaining clip utilized in conjunction with the mold.
Figure 9:
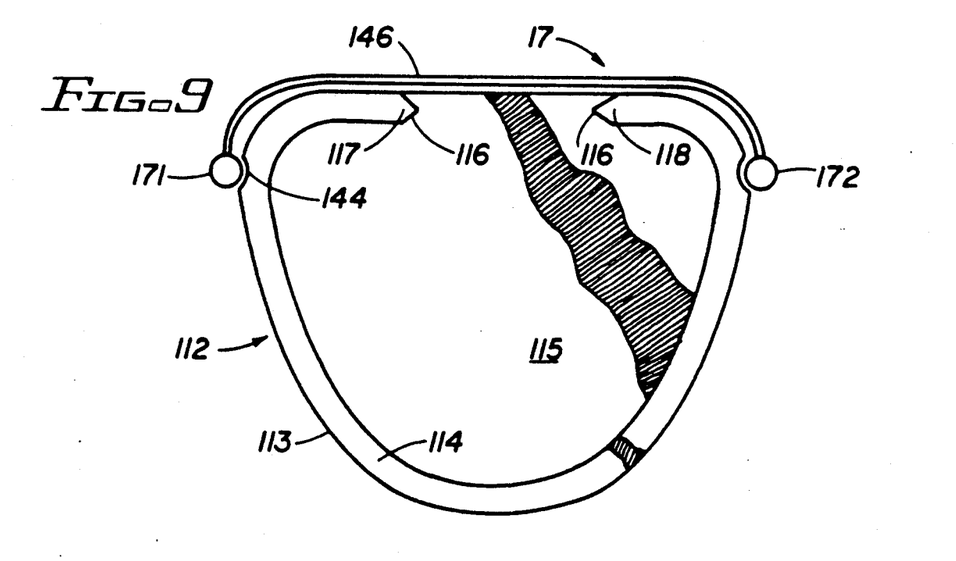
FIG. 9 is a top view of the mold and clip of FIG. 8.

In use of the apparatus of the invention, the mold 112 is first utilized to produce the working part of the dental model. The working part of the dental model is the part from which the dental technician ordinarily will cut one of the replicas of the teeth in order to prepare a crown or a bridge. The working model includes pins which are inserted in the positive cast or replica of the teeth of the upper or lower jaw of a patient. As is well known, this positive cast is made using a negative cast of the teeth which is prepared by the dentist and forwarded to the dental technician. In some instances a dentist may make both the negative and positive casts, but ordinarily, the technician makes the positive cast. After the positive cast is made, holes are drilled from the bottom of the cast up beneath the tooth or teeth for which a crown or bridge will be made. Pins are glued in these holes and extend outwardly from the holes and from the bottom of the positive cast. The pins and selected parts of the bottom of the positive cast are coated with a material which dries and facilitates the sliding removal of the pins and parts of the positive cast from the yellow gypsum casting stone which will form the base of the working model. After all of the appropriate pins are inserted in the positive cast of the upper or lower teeth, as the case may be, the positive cast is ready to be anchored in the base of the working model. To accomplish this, the mold 112 of FIGS. 8 and 9 is taken and means 70 is inserted in opening 116 in the manner indicated in FIGS. 6 and 7. The positive cast is inserted in the mold 112 with the bottoms of the pins extending out from the positive cast contacting substrate 115 and with the cusps of the teeth in the positive cast pointing upwardly away from substrate 115. For the purposes of the remainder of this example, it is assumed that the positive cast in the working model is of a patient's lower teeth. After the positive cast of the lower teeth is inserted and generally centered in mold 112, a hardenable yellow colored gypsum stone mixture is poured into the cavity of mold 112 and permitted to harden. The stone fills the mold 112 up to edge 114, and covers the portions of the pins extending out from the bottom of the positive cast. The stone also covers the bottom of the positive cast. After the yellow stone hardens, the flexible mold 112 is peeled off of the stone and means 70 is slidably displaced in a direction away from substrate 115 to slide grooves 130 and 131 along edges 117 and 118 to remove means 70 from opening 116. When the yellow stone is poured into mold 112, the mold is, as noted, filled up to the edge 114 and anchor means 124 is covered by the stone. Consequently, when the stone hardens, means 124 is embedded in the stone. The threads on anchor means 124 permit, however, a rotational torque to be applied to member 122 so that means 124 can be turned out of the stone base and reused. Small flanges 160 can be formed which extend from member 122 to anchor means 124 (FIG. 10). These flanges make it more difficult to rotate member 122 and reduce the likelihood that means 70 will be inadvertently loosened from the yellow stone base in which anchor means 124 is embedded. The yellow stone base 180 with means 70 attached thereto is illustrated in FIGS. 6 and 7. Dashed lines 112, 113, 114, etc. in FIG. 6 illustrate the position of mold 112 about base 180 before the flexible mold is peeled off of hardened base 180 and means 70 is simultaneously upwardly slid free of opening 116. In FIG. 6 the positive cast or replica of the lower teeth is indicated by reference character 81. The positive cast of the lower teeth and of gums 82 is, for the purpose of clarity, omitted from FIG. 7.

After the working part of FIG. 6 is produced, a positive cast of the patient's upper teeth is produced. The cast of the upper teeth is placed on cast 81 of the working part to accurately register the cusps of the upper replica teeth with the cusps of the lower replica teeth and reproduce the patient's bite. Small amounts of a removably sticky wax are applied to the registered upper and lower teeth in the positive casts of the same. This wax holds the positive cast of the upper teeth in the desired position against the positive cast of the lower teeth. Therefore, an intermediate model assembly is produced which includes the working part of the dental model and includes the positive cast of the upper teeth affixed to the cusps of the lower teeth replicas of the working part of the dental model. The cusps of the upper replica teeth are held by wax in registration with the cusps of the lower replica teeth. On completion of this intermediate model assembly, the opposing part of the dental model is prepared.

In preparing the opposing part of the dental model, the mold 112 of FIGS. 8 and 9 is taken and means 121, block 150, and posts 136 and 137 are positioned on the mold 112 in the manner shown in FIG. 5. The intermediate model assembly is mounted by sliding grooves 130 and 131 of means 70 intermediate the upper ends of posts 136 and 137 downwardly in the direction of arrow R. When means 70 is slid intermediate the upper ends of posts 136 and 137, set screws 138 and 139 are appropriately tightened to solidify the block 150—post 136—post 137—means 121—means 70 assembly. Means 70 is inserted intermediate posts 136 and 137 such that the working part of the dental model is upside down and such that the teeth point downwardly toward substrate 115. Consequently, in the positive cast of the upper teeth contained in the intermediate model assembly, the replicas of the upper teeth point upwardly. Further, since the cusps of the replicas of the upper teeth are, as earlier noted, attached to the cusps of the replicas of the lower teeth in the working part, the positive cast of the upper teeth is suspended above substrate 115. The lowermost portion of the positive cast of the upper teeth (which lowermost portion normally reproduces the gums surrounding the upper teeth) is suspended in position above substrate 115 and above the upper edge 114 of sidewall 113. A hardenable yellow gypsum stone is poured into mold 112. Sufficient stone is poured into mold 112 to fill mold 112 up to edge 114 and cover anchor means 124. Before the stone hardens, set screws 138 and 139 are slightly loosened, if necessary, and means 70 is pressed to slowly downwardly slide member 70 along posts 136 and 137 in the direction of arrow R until the lowermost portion of the positive cast of the upper teeth contacts and sinks into the soft yellow stone in mold 112 a distance of about one eighth of an inch. The positive cast of the upper teeth lies within the perimeter of mold 112 defined by edge 114. Set screws 138 and 139 are appropriately tightened to maintain means 70 at the elevation at which the lowermost portion of the positive cast of the upper teeth extends about one eighth of an inch, or any other desired distance, into the soft yellow stone in mold 112. The yellow stone is then permitted to harden. While the stone hardens, means 70 and 121 are maintained in parallel relationship by posts 136 and 137. The wax interconnecting the tips of the upper and lower teeth replicas in the positive casts of the upper and lower teeth maintains the cusps of the teeth replicas in proper bite registration.

After the yellow stone in mold 112 hardens, it forms the base of the opposing part of the dental model. The stone in mold 112 covers anchor means 124 of the attachment means 121 and embeds anchor means 124 in the stone. The lowermost portion of the positive cast of the upper teeth is anchored in the base of the opposing part. The apparatus of FIG. 5 is disassembled by loosening set screws 138 and 139 and slidably upwardly pulling posts 136 and 137 and block 150 free from means 70 and 121. Flexible mold 112 is peeled away from the hardened base of the opposing part of the dental model while means 121 is slidably removed from opening 116 by upwardly displacing means 121 away from substrate 115 in the direction of arrow P in FIG. 5. Clip 170 can be removed from mold 112 to facilitate removal of mold 112 from the hardened stone base of the opposing part of the dental model. After mold 112 is removed from the hardened base of the opposing part of the dental model and after block 150 and posts 136 and 137 are removed from contact with means 70 and 121, all that remains is the dental model. The dental model includes the working part and the opposing part. The tips of the teeth of the working part are held in registration with and against the tips of the teeth of the opposing part by the wax earlier applied in the process. The wax can be removed before or after the work part and opposing part are mounted on the dental articulator of FIGS. 1 to 4.

As indicated in FIGS. 1 and 6, the working model is affixed to the articulator by placing attachment means 70 adjacent forward portion 53. Nubs 71 and 72 fit into openings 62 and 63, respectively, and the shank 65 is threaded into an internally threaded opening 125 formed in connector member 122 (FIGS. 6 and 7). Attachment means 121 is similarly attached to forward portion 52 by threading the shank 200 (FIG. 2) of a screw through slot 58 into an internally threaded aperture 125 formed in attachment means 121 Nubs 71 and 72 on attachment means 121 are received by openings 55 and 54, respectively. When means 70 and 121 are affixed to portions 52 and 53, flat planar faces 52A and 53A are maintained in a common flat plane. The vertical distance between portions 52 and 53 can be adjusted by loosening knobs 43, sliding shafts 44 in sleeves 41, and then tightening knobs 43. The articulator of FIG. 1 therefore permits means 70 and 121 to be mounted thereon while maintaining the orientation of means 70 with respect to means 121 which was maintained in the molding apparatus of FIG. 5.

Openings 62 and 63 are provided on portion 52 to enhance the vertical adjustment capability of the articulator of FIG. 1. At times positive casts are prepared which replicate only the teeth and replicate little if any of the gums extending downwardly from the teeth. These "short" positive casts tend to produce working and opposing parts which are spaced unusually close together. Opening 56 and 57 compensate for such closely spaced working and opposing parts.

Having described my invention in such terms as to enable those skilled in the art to understand and practice it, and having identified the presently preferred embodiments thereof, I claim:

1. A dental articulator for a dental model, the dental model including:
   a lower part including replications of the lower teeth of a patient's mouth, and
   an upper part including replications of the upper teeth of a patient's mouth,
   said articulator including:
   (a) base means including a forward portion shaped and dimensioned to receive the lower part of the dental model;
   (b) an upper member including a forward portion shaped and dimensioned to receive the upper part of the dental model, said upper member having first and second operative positions;
   (c) connecting means for interconnecting said base means and said upper member in spaced apart relationship, said connecting means including:
   (i) at least one support arm attached to and outwardly extending from said base means,
   (ii) shaft means extending from said support arm, spaced apart from said base means, and having a longitudinal axis spaced apart from said forward portion of said upper member,
   (iii) a slot formed in said upper member, slidably engaging said shaft means, and having a back inner stop portion, and
   (iv) spring means interconnecting said upper member and said shaft means, said spring means extending outwardly from said shaft means and having a selected load to hold said upper member in said first operative position with said back inner stop portion of said slot against at least one of the pair consisting of said spring means and said shaft means;
   said slot and said shaft means being shaped and dimensioned such that when a lateral force generally parallel to and spaced apart from said longitudinal axis of said shaft means and having a selected magnitude is applied to said forward portion of said upper member, a torque is produced on said upper member which causes:

(d) said upper member to move from said first operative position to said second operative position;
   (e) said slot to pivot with respect to and slide over said shaft means and at least a portion of said stop portion to move away from said shaft means; and,
   (f) the loading of said spring means to be altered.

2. The dental articulator of claim 1 wherein said upper member has a third operative position and said slot and shaft means are shaped and dimensioned such that when a transverse force:

acting in a direction perpendicular to said lateral force,
   acting in a direction perpendicular to and spaced apart from said longitudinal axis of said shaft means, and
   having a selected magnitude, is applied to said forward portion of said upper member,
   (a) a rotational torque is produced acting on said upper member;
   (b) said upper member rotates around said longitudinal axis from said first operative position to said third operative position; and,
   (c) load on said spring means is not altered.

3. The dental articulator of claim 1 wherein said upper member has a fourth operative position and said slot and shaft means are shaped and dimensioned such that when a displacement force:

acting in a direction perpendicular to said transverse force,
   acting in a direction perpendicular to, toward, and passing through said longitudinal axis of said shaft means, and
   having a selected magnitude, is applied to said forward portion of said upper member,
   (a) said forward portion is pushed toward said longitudinal axis;
   (b) said upper member moves from said first operative position to said fourth operative position; and,
   (c) the loading of said spring means is altered.

4. Molding apparatus for forming an opposing part of a dental model, the dental model including the opposing part and a working part, the opposing part including:

a base, and,
   affixed to the base, replications of one of a pair of sets of teeth in the group consisting of the upper set of teeth in a patient's mouth and the lower set of teeth in the patient's mouth,
   a working part including:
   a base, and affixed to the base of the working part, replications of the other of the pair of sets of teeth in the group consisting of the upper set of teeth in a patient's mouth and the lower set of teeth in the patient's mouth,
   the opposing and working parts being attached to an articulator, the articulator comprising:
   base means including a forward connector portion shaped and dimensioned to detachably receive the lower part of the dental model,
   an upper member including a forward connector portion shaped and dimensioned to detachably receive the upper part of the dental model, and
   connector means for interconnecting said base means and said upper member in spaced apart relationship, said molding apparatus including:
   (a) a mold for forming from a pourable hardenable compound deposited therein said base of the lower part of the dental model, said mold including:
      (i) a sidewall for defining the perimeter of a mold cavity and having an upper edge for defining the opening to the mold cavity,
      (ii) a substrate extending across the space intermediate said sidewall and defining the bottom of the mold cavity, and,
      (iii) an opening formed in said sidewall;
   (b) first attachment means including:
      (i) a connector member shaped and dimensioned to be inserted in said opening,
      (ii) anchor means extending from said connector member within the perimeter of the mold cavity to be at least partially covered by and to engage pourable hardenable compound poured in the mold cavity, and
      (iii) means for detachably connecting said first attachment means to said forward connector portion of one of the pair consisting of said base means and said upper member of said articulator;
   (c) at least one elongate positioning post having a longitudinal axis and a lower end and an upper end, said lower end being received by and anchored in an opening formed in the group consisting of said side wall, said substrate, and said first attachment means;
   (d) dental model means including:
      (i) the working part of the dental model,
      (ii) said one of said pair of sets of teeth removably affixed to said other of said pair of sets of teeth to duplicate the bite between said one and said other of said pair of sets of teeth, and
      (iii) second attachment means attached to said base of the working part and shaped and dimensioned to slidably engage and move down said positioning post
         while maintaining said base of the working member in a selected orientation with respect to said bottom of the mold cavity,
         while maintaining said one of said sets of teeth above said bottom of the mold cavity and intermediate said bottom and the working part of said model means, and
         to imbed a portion of said one of said pair of sets of teeth in hardenable compound poured in said mold, said one of said pair of sets of teeth being anchored in said compound when said compound hardens.

5. The molding apparatus of claim 4, wherein said connector means includes means for adjusting the distance between said forward portion of said upper member and said forward portion of said base means.

6. The molding apparatus of claim 5, wherein said molding apparatus is shaped and dimensioned such that while said second attachment means moves down said positioning post the distance between said second attachment and said first attachment means changes, but the orientation of said second attachment means with respect to said first attachment means otherwise remains unchanged.

7. The molding apparatus of claim 5, wherein said molding apparatus is shaped and dimensioned such that after said one of said pair of sets of teeth is imbedded in said hardenable compound and said compound hardens, (a) the working model and the opposing model can be removed from said molding apparatus;

(b) said first attachment means can be connected to said forward portion of said base means; and (c) said second attachment means can be connected to said forward portion of said upper member;

with said one of said pair of sets of teeth removably affixed to said other of said pair of sets of teeth to duplicate the bite between said one and said other of said pair of sets of teeth.

* * * * *